(12) United States Patent
McIntyre (10) Patent No.: US 7,892,751 B2
(45) Date of Patent: Feb. 22, 2011

(54) METHOD OF DETECTING OR DIAGNOSING OF A NEURODEGENERATIVE DISEASE OR CONDITION

(75) Inventor: John A. McIntyre, Indianapolis, IN (US)

(73) Assignee: Redox-Reactive Reagents LLC, Beech Grove, IN (US)

(*) Notice: Subject to any disclaimer, the term of this patent is extended or adjusted under 35 U.S.C. 154(b) by 0 days.

(21) Appl. No.: 11/359,489

(22) Filed: Feb. 23, 2006

(65) Prior Publication Data

US 2006/0141541 A1    Jun. 29, 2006

Related U.S. Application Data

(63) Continuation-in-part of application No. 11/108,826, filed on Apr. 19, 2005, which is a continuation-in-part of application No. 10/863,365, filed on Jun. 9, 2004, now Pat. No. 7,368,542.

(60) Provisional application No. 60/476,607, filed on Jun. 9, 2003.

(51) Int. Cl.
G01N 33/53 (2006.01)
A61K 35/30 (2006.01)
C07K 16/00 (2006.01)

(52) U.S. Cl. .................. 435/7.1; 424/570; 530/387.1

(58) Field of Classification Search .................. None
See application file for complete search history.

(56) References Cited

U.S. PATENT DOCUMENTS

| | | |
|---|---|---|
| 4,703,001 A | 10/1987 | Vodian et al. |
| 4,950,612 A | 8/1990 | Khanna et al. |
| 5,061,790 A | 10/1991 | Elting et al. |
| 5,939,394 A | 8/1999 | Fleming et al. |
| 5,980,954 A | 11/1999 | Bolton |
| 6,660,267 B1 | 12/2003 | Carroll |
| 6,932,969 B1 | 8/2005 | Bourel et al. |
| 7,195,881 B2 | 3/2007 | Geffard |
| 2004/0082015 A1 | 4/2004 | Geffard |
| 2005/0101016 A1 | 5/2005 | McIntyre |
| 2005/0260681 A1 | 11/2005 | McIntyre |

FOREIGN PATENT DOCUMENTS

| | | |
|---|---|---|
| EP | 0 778 025 B1 | 6/1997 |
| JP | 502580/1990 | 8/1990 |
| JP | 517302/2000 | 12/2000 |
| WO | WO 89 05975 | 6/1989 |
| WO | WO 98/07436 | 2/1998 |
| WO | WO 00/74717 | 12/2000 |
| WO | WO 2004/111608 | 12/2004 |

OTHER PUBLICATIONS

Robertson and Greaves, Blood Rev 20: 201-212, 2006.*
Gallo et al. J Neurol Sc 122: 97-101, 1994.*
Tanne et al. Curr Rheumat Rep 3: 286-292, 2001.*
Jedryka-Goral et al. Clin Rheumatol 19: 306-310, 2000.*
Mosek et al. Dem Ger Cog Disorder 11: 36-38, 2000.*
Oomen et al. Psychiat Res 58: 83-88, 1995.*
Gomez-Puerta et al. Rheumatol 44: 95-99, 2005.*
Sokol et al., Neurology 55:1379-1381, 2000.*
Martinez-Cordero et al., J Invest Allergol Clin Immunol 7: 596-601, 1997.*
McIntyre et al., Ann NY Acad Sci 1109: 296-302, 2007.*
Sokol et al., Ped Neurol 39: 293-294, 2008.*
Ischiropoulos et al. J Clin Invest 111: 163-169, 2003.*
Ischiropoulus, Harry et al, "Oxidative Stress and Nitration in Neurodegeneration: Cause, effect, or association?", *J. Clin. Invest.* 2003 111:pp. 163-169.

(Continued)

*Primary Examiner*—Jeffrey Stucker
*Assistant Examiner*—Aditi Dutt
(74) *Attorney, Agent, or Firm*—Antonelli, Terry, Stout & Kraus, LLP.

(57) ABSTRACT

A neurodegenerative disease or condition is diagnosed in a subject by obtaining a sample of cerebral spinal fluid from the subject and assaying the sample by an assay method that detects the presence of at least one antiphospholipid autoantibody in the sample, wherein an elevated level of at least one antiphospholipid autoantibody in the sample of cerebral spinal fluid correlates with a neurodegenerative disease or condition in the subject. The neurodegenerative disease or condition may also be diagnosed by assaying a sample of cerebral spinal fluid to detect nitrosylated antibodies, wherein an elevated level of nitrosylated antibodies correlates with a neurodegenerative disease or condition in said subject. A neurodegenerative disease or condition is also detected or diagnosed by assaying a first sample of cerebral spinal fluid from the subject to determine a level of at least one autoantibody having a selected specificity, treating a second sample of cerebral spinal fluid with an oxidizing agent and assaying the oxidized second sample to determine a level the at least autoantibody having the selected specificity, and comparing the level of the at least one autoantibody in the first sample with the level of the at least one autoantibody in the oxidized second sample, wherein a lack of increase in the level of the at least one autoantibody in the oxidized second sample as compared to the level of the at least one autoantibody in the first sample correlates with a neurodegenerative disease or condition in said subject.

9 Claims, 3 Drawing Sheets

OTHER PUBLICATIONS

Smith, Mark A., et al, "Widespread Peroxynitrite-Mediated Damage in Alzheimer's Disease", *J. Neuroscience*, Apr. 15, 1997, 17(8) pp. 2653-2657.

McIntyre, John A., "The Appearance and Disappearance of Antiphospholipid Autoantibodies Subsequent to Oxidation-reduction Reactions", *Thrombosis Research* 2004, 114, pp. 579-587.

McIntyre, John A., et al, "Autoantibodies Unmasked by Redox Reactions", *J. Autoimmun* 2005; 24 pp. 311-317.

McIntyre, John A., et al "Redox-reactive Autoantibodies: Detection and Physiological Relevance", *Autoimmunity Reviews* 2008; 5 pp. 76-83.

Sokol, D.K. et al, "Testing for Antiphospholipid Antibody (aPL) Specificities in Retrospective 'Normal' Cerebral Spinal Fluid (CSF)", *Clin Develop. Immunol*. 2005; 11: pp. 7-12.

Adams, J. Paige et al, "Molecular Psychology: Roles for the ERK MAP Kinase Cascade in Memory", *Annu. Rev. Pharmacol. Toxicol*. 2002 42 pp. 135-163.

Hindley, Alison et al, "Extracellular Signal Regulated Kinase (ERK)/mitogen Activated Protein Kinase (MAPK)-Independent Functions of Raf Kinases", *J. Cell Science*, 2002; 115, pp. 1575-1581.

Cheung et al, "Emerging Role for ERK as a Key Regulator of Neuronal Apoptosis", *Science*, 2004; 251: pp. 1-3.

Chapman, J. et al, "Antiphospholipid Antibodies Permeablizie and Depolarize Brain Synaptoneurosomes", *Lupus* 1999; 8: pp. 127-133.

D'Aandrea, PhD, Michael R., "Evidence that Immunoglobulin-positive Neurons in Alzheimer's Disease are Dying Via the Classical Antibody-dependent Complement Pathway", *Am. J. Alzheimer's Dis. Other Dimentas* 2005; 20; pp. 144-150.

Colucci-D'Amato, L. et al, "Chronic Activation of ERK and Neurodegenerative Diseases", *Bioassays*, 2003: 25; pbs. 1085-1095.

John McIntyre, The Appearance and Disappearance of Antiphospholipid Autoantibodies Subsequent to Oxidation-Reduction Reactions, Thrombosis Research 2004, 114, pp. 579-587.

www.ucsfhealth.org/childrens/edu/bottleWeaning.html , provided by UCSF Children's Hospital, Patient Education, Baby Bottle Weaning, 2002-2007.

J. Cabiedes et al., Hidden Anti-Phospholipid Antibodies in Normal Human Sera Circulate as Immune Complexes Whose Antigen can be Removed by Heat Acid, Hypermolar Buffers or Phospholipase Treatments, Eur. J. Immunol. pp. 2108-2114, 1998.

Office Action of Patent Office of the People's Republic of China Application No. 200480015987.9 dated Feb. 6, 2009.

Office Action of Japanese Patent Application No. 515229/2006 dated Dec. 16, 2008.

EP Office Action dated App. No. 04 754 487.9 dated Mar. 5, 2009.

International Preliminary Report on Patentability, PCT/US2007/001582, Aug. 22, 2008.

International Search Report/Written Opinion, PCT/US2007/001582, Dec. 4, 2007.

International Search Report/Written Opinion, PCT/US2006/12802, Jan. 7, 2008.

Gallo, et al., Cerebrovascular and neurological disorders associated with antiphospholipid antibodies in CSF and serum, Journal of the Neurological Sciences, 122 (1994).

Mosek, et al., Dementia and Antiphospholipid Antibodies, Dementia and Geriatric cognitive disorders, Jan./Feb. 2000, 11,1, ProQuest Central, pp. 26-38.

Tanne, MD, et al., Neurological Manifestations of the Antiphospholipid Syndrome, Current Theumatology Reports 2001, 3:286-292, Current Science Inc.

Teunissen, et al., Biochemical markers related to Alzheimer's dementia in serum and cerebrospinal fluid, Neurobiology of Aging 23 (2002, pp. 485-508.

Nagababu, et al., Formation of Fluorescent Heme Degradation Products during the Oxidation of Hemoglobin by Hydrogen Peroxide, Biochemical and Biophysical Research Communications, 247, 1998, pp. 592-596.

Hood, et al., Immunology, $2^{nd}$ Edition, Chapter 9, Immune Effector Mechanisms and the Complement System, The Benjamin/Cummings Publishing Company, Inc., 1984.

Pauling, Linus, General Chemistry: An Introduction to Descriptive Chemistry and Modern Chemical Theory, $2^{nd}$ Edition, W.H. Freeman and Company, p. 523.

Australian Office Action, Australian Patent Application No. 2007225434, Aug. 24, 2009.

European Office Action, European Patent Application No. 07 749 017.5, Jan. 5, 2010.

Supplementary European Search Report, European Application No. 07 749 017.5, Dec. 3, 2009.

Indian Office Action, Indian Application No. 4760/CHENP/2007.

Supplementary Partial European Search Report, European Application No. 04 75 4487, Jun. 19, 2006.

EPO Communication pursuant to Article 94(3) EPC, EP Application No. 04 754 487.9, Jul. 24, 2007.

EPO Communication pursuant to Article 94(3) EPC, EP Application No. 04 754 487.9, Apr. 9, 2008.

EPO Communication pursuant to Article 94(3) EPC, EP Application No. 04 754 487.9, Aug. 14, 2009.

EPO Communication pursuant to Article 94(3) EPC, EP Application No. 04 754 487.9, Mar. 5, 2009.

EPO Communication pursuant to Article 94(3) EPC, EP Application No. 04 754 487.9, May 7, 2010.

Supplementary European Search Report, EP Application No. 07 749 017.5, Dec. 3, 2009.

McIntyre, et al., Redox-Reactive Antiphospholipid Antibody Differences Between Serum From Alzheimer's Patients and Age-Matched Controls, Autoimmunity, Informa Healthcare, Dec. 18, 2009, pp. 1-7.

\* cited by examiner

Figure 3A
Control CSF

Figure 3B
Alzheimer's CSF

METHOD OF DETECTING OR DIAGNOSING OF A NEURODEGENERATIVE DISEASE OR CONDITION

The present application is a continuation-in-part of U.S. patent application Ser. No. 11/108,826, filed on Apr. 19, 2005, which application is a continuation-in-part of Ser. No. 10/863,365, filed Jun. 9, 2004, U.S. Pat. No. 7,368,542, which application claims the benefit of U.S. Provisional Application Ser. No. 60/476,607, filed Jun. 9, 2003, the entire contents of which applications are incorporated by reference herein.

FIELD OF INVENTION

The present invention relates to methods of detecting or diagnosing a neurodegenerative disease or condition. In particular, the aspects of the present invention relate to methods of assaying cerebral spinal fluid of a subject to determine the presence or absence of autoantibodies.

BACKGROUND OF THE INVENTION

A continuing problem in the diagnosis of neurodegenerative diseases or conditions such as Alzheimer's has been to devise a reliable biomarker that provides a definitive indication of a physical pathology. Typically, a neurodegenerative disease is diagnosed based on behavior, signs of cognitive impairment, and various forms of radiological imaging, and a definitive diagnosis is obtained only upon autopsy.

Further, the cause of neurodegenerative diseases has been a mystery, making it difficult to know what biological factors to look for in terms of early warning signs that a neurodegenerative disease may be present. Post mortem analysis of brain tissue appears to implicate metal ions in neurodegenerative diseases. Proteins associated with these diseases bind metals as part of their normal function, but in neurodegenerative diseases, something causes the proteins to not fold around the metals properly, thereby revealing transition metal sites that can participate in oxidation-reduction reactions. This development leads to mild to severe amyloid angiopathy.

In neurodegenerative diseases such as Alzheimer's, Parkinson's Huntington's amyotrophic lateral sclerosis (ALS) and scrapie, oxidative modifications occur leading to pathological lesions. For example, tyrosine nitration is one of the earliest markers found in Alzheimer's disease brains and ALS. (Ischiropoulos, I. & Beckman, J S. "Oxidative stress and nitration in neurodegeneration: cause, effect, or association?" *J. Clin. Invest.* 2003; 111:163-69.) One of the most likely oxidants involved in nitrosylation of tyrosines in the central nervous system is derived from nitric oxide reacting with superoxide, called peroxynitrite. (Smith, M A, et al. "Widespread peroxynitrite-mediated damage in Alzheimer's disease." *J. Neuroscience.* 1997; 17:2653-57)

The present inventor has previously reported the discovery that blood and other bodily fluids from normal individuals contain a significant number of antibodies, that, when treated with an oxidizing agent, become capable of binding self antigens. See, for example, the following publications:

McIntyre, J A. "The appearance and disappearance of antiphospholipid antibodies subsequent to oxidation-reduction reactions." *Thromb. Res.* 2004; 114:579-87.

McIntyre, J A, Wagenknecht, D R, & Faulk, W P. "Autoantibodies unmasked by redox reactions." *J. Autoimmun* 2005; 24:311-17.

McIntyre, J A, Wagenknecht, D R, & Faulk, W P. "Redox-reactive autoantibodies: Detection and physiological relevance. *Autoimm. Rev.* 2006; 5:76-83. and U.S Patent Application Publication No. 2005/0101016 A1.

The entire contents of these publications are incorporated herein by reference.

Such autoantibodies may be detected by treating the blood or other bodily fluid with an oxidizing agent and then using a screening assay to detect antibodies that bind a self antigen. It has been found that such autoantibodies are present in blood or other bodily fluids in a wide variety of isotypes and specificities. It has also been found that autoantibodies can be detected in a purified or fractionated immunoglobulin composition that has been treated with oxidizing conditions. Since the autoantibodies are not detected above a minimal baseline in blood or other bodily fluids from normal individuals or in immunoglobulin compositions pooled from normal individuals in the absence of an oxidation step, antibodies or autoantibodies having this property are referred to herein as "masked" antibodies or "masked" autoantibodies, and the process of treating blood or other bodily fluids or immunoglobulin preparations with oxidizing conditions is referred to herein as "unmasking" the masked antibodies or autoantibodies. Antibodies having the property of becoming masked or unmasked, depending on oxidation-reduction conditions may also be referred to herein as "redox antibodies".

To date, masked autoantibodies that have been detected in the blood of normal individuals include the following:

TABLE

Masked autoantibodies identified to date after redox conversion of normal plasma or IgG.
Current list of redox-reactive autoantibodies*

Antiphospholipid antibodies, aPS, aCL, aPE, aPC, Lupus Anticoagulant (LA)
Anti-glutamic acid decarboxylase (GAD)
Anti-tyrosine phosphatase (IA-2)
Anti-nuclear antibodies (ANA)
Anti-cell organelles: nucleolus, lamin, Golgi, etc.
Anti-granulocytes: neutrophils, monocytes
Anti-B lymphocyte
Anti-myeloperoxidase
Anti-tumor cells lines: Raji, Jurkat, U87MG, K562
Anti-trophoblast and trophoblast basement membranes (TBM)
Anti-factor VIII
Anti-PF4/heparin complex
Anti-$\beta_2$-glycoprotein I
Anti-RBC (broad reactivity)

*Additional specificities are anticipated upon further testing.
Table abbreviations used:
aCL, anticardiolipin
aPC, antiphosphatidylcholine
aPE, antiphosphatidylethanolamine
aPS, antiphosphatidylserine
APPT, activated partial thromboplastin time
dRVVT, dilute Russell's viper venom time
ELISA, enzyme-linked immunosorbant assay The present inventor has proposed that nitrosylation of tyrosine residues in and around the antibody hypervariable region may be a potential mechanism for antibody masking and unmasking. A change in nitration could produce conformational changes in an antibody binding site that result in alteration of the binding specificity of the antibody. To test this theory, hemin-treated and untreated samples of IgG were assayed for nitrated tyrosines and it was found that there was significant IgG nitrosylation after hemin exposure. See McIntyre, *J. Autoimmun*, cited above.

It is presumed that masked autoantibodies present in normal individuals do not cause harm to the normal individual, and may even play a yet unknown beneficial role. However, autoantibodies that become unmasked in the body, which can occur through physiological oxidative reactions, are believed to play a role in autoimmune diseases.

The present inventor has also reported the discovery of masked autoantibodies in samples of cerebral spinal fluid taken from normal individuals. See U.S. patent application Ser. No. 11/108,826; Sokol, D K, Wagenknecht, D R & McIntyre, J A. "Testing for antiphospholipid antibody (aPL) specificities in retrospective "normal" cerebral spinal fluid (CSF)". *Clin. Develop. Immunol.* 2004; 11:7-12. As with autoantibodies detected in the blood, the autoantibodies in cerebral spinal fluid from normal individuals can be detected in surprisingly large quantities by treating the cerebral spinal fluid sample with oxidizing conditions, such as with an oxidizing agent or the use of electromotive force and then using a screening assay to detect antibodies that bind self antigens. Such autoantibodies are not detected above a minimal baseline in the cerebral spinal fluid taken from a normal individual that is not subjected to oxidizing conditions. Here again, it can be presumed that autoantibodies that may be present in cerebral spinal fluid of a normal individual in their masked form do not cause harm to the individual, and may play a yet unknown beneficial role; however, it is apparent that the autoantibodies could cause damage if they were to become unmasked in the cerebral spinal fluid. These results suggested that autoantibodies may be involved in neurodegenerative diseases such as Alzheimer's and Parkinson's diseases, and that these diseases could be triggered or aggravated by unmasking of masked autoantibodies in the cerebral spinal fluid. This theory is supported by the discovery, discussed above, that metal ions are implicated in neurodegenerative diseases. For example, if transition metal sites are exposed by protein misfolding, such exposed sites could promote oxidation-reduction reactions that lead to unmasking of autoantibodies. Unmasked antibodies such as antiphospholipid autoantibodies can interact with phospholipids and phospholipid-binding proteins in brain cells and may therefore cause many of the lesions and shrinkage of the brain that are seen in MRI studies of the Alzheimer patient brains and can cause the physical damage seen in other types of neurodegenerative diseases.

As reported herein, it has now been discovered that autoantibodies are not detected in the post mortem cerebral spinal fluid of Alzheimer's patients subsequent to oxidizing reactions. In contrast, post mortem control cerebral spinal fluid samples from patients with no history of neurodegenerative diseases do possess autoantibodies subsequent to oxidation reactions. These results suggest that certain neurodegenerative diseases or conditions can be characterized by detecting the presence of active or unmasked autoantibodies in cerebral spinal fluid. Moreover, as further discussed herein, it has been discovered that cerebral spinal fluid of confirmed Alzheimer patients that is treated with an oxidizing agent such as hemin does not show a dramatic increase in the amount of detectable autoantibodies, as compared with untreated cerebral spinal fluids, which indicate that an unmasking process has occurred in a diseased subject, such that the level of masked autoantibodies becomes depleted. These results alternatively suggest that the presence of a neurodegenerative disease or condition can be detected by comparing the amount of autoantibodies in a sample of cerebral spinal fluid that is untreated with the sample of cerebral spinal fluid that is treated with an oxidizing agent such as hemin or electromotive force.

In addition to the discovery that Alzheimer's post mortem cerebral spinal fluid lacks redox-reactive autoantibodies, it has been shown that the autoantibodies unmasked in cerebral spinal fluid from a normal individual can stimulate signal transduction reactions when assayed using a mouse synaptosome model. This finding may relate to the brain pathology observed in neurodegenerative diseases at autopsy since the unmasked autoantibodies from an individual have been shown to phosphorylate the extracellular signal regulated kinase (ERK1/2), a member of the mitogen activated protein kinase (MAPK) cascade. Such phosphorylation reactivity either in the cytosol and/or the nucleus can promote gene expression leading to proliferation, transformation, and differentiation or programmed cell death (apoptosis). Related phosphorylation pathways, for example, JNK and p38 also would be expected to participate. Apoptosis of neurons as well as interference with memory and motor functions in the brain subsequent to ERK1/2 phosphorylation are known responses resulting from activation of this stimulation pathway. (For review, references to ERK1/2 phosphorylation outcomes are found in: Adams, JP and Sweatt, J D. "Molecular Psychology: Roles for the ERK MAP Kinase Cascade in Memory". *Annu. Rev. Pharmacol. Toxicol.* 2002; 42:135-63; Hindley, A, and in, Kolch, W. "Extracellular signal regulated kinase (ERK)/mitogen activated protein kinase (MAPK)-independent functions of Raf kinases". *J. Cell Science,* 2002; 115:1575-81 and in, Cheung, ECC and Slack, R S. "Emerging Role for ERK as a Key Regulator of Neuronal Apoptosis". *Science,* 2004; 251:1-3). A direct pathogenic role for antiphospholipid antibodies has also been shown in: Chapman, J, et al. "Antiphospholipid antibodies permeabilize and depolarize brain synaptosomes". *Lupus* 1999; 8:127-33.

It is proposed that the failure to find redox-reactive autoantibodies in Alzheimer's disease cerebral spinal fluid is due to their depletion caused by disease-associated nitrosylation of proteins that are characteristic of certain neurodegenerative diseases. The autoantibodies are not detected because they have targeted and are bound to the neurons in the diseased brain. Recent evidence for antibody deposition in the brain cells can be found in: DeAndrea, M R. "Evidence that immunoglobulin-positive neurons in Alzheimer's disease are dying via the classical antibody-dependent complement pathway". *Am J Alzheimer's Dis Other Dimentias.* 2005; 20:144-50. Moreover, chronic activation of ERK1/2 is supported by failure to detect redox-reactive autoantibodies in Alzheimer's cerebral spinal fluid subsequent to oxidation. That this can lead to neurodegenerative diseases was reported by: Colucci-D'Amato L, et al. "Chronic activation of ERK and neurodegenerative diseases". *Bioassays,* 2003; 25:1085-95.

SUMMARY OF THE INVENTION

Aspects of the present invention provide a method of detecting or diagnosing a neurodegenerative disease or condition in a subject. Further aspects of the invention provide a method of monitoring a subject over a period of time to detect the development or progress of a neurodegenerative disease or condition.

These and other objectives are achieved by a method of detecting or diagnosing a neurodegenerative disease or condition in a subject by obtaining a sample of cerebral spinal fluid from the subject and assaying the sample to determine the presence or absence of autoantibody in said sample, wherein an elevated presence of autoantibody and/or the lack of redox-reactive autoantibodies correlates with a neurodegenerative disease or condition in said subject.

The objectives are further achieved by a method of detecting or diagnosing a neurodegenerative disease or condition in a subject by assaying a sample of cerebral spinal fluid from a subject to determine an extent of nitrosylation of the antibodies, wherein an elevated extent of nitrosylation of antibodies correlates with a neurodegenerative disease or condition in said subject.

The objectives are further achieved by a method of detecting or diagnosing a neurodegenerative disease or condition in a subject by assaying first sample of cerebral spinal fluid from the subject to determine a level of at least one autoantibody of a selected specificity, treating a second sample from the subject with an oxidizing agent and assaying the oxidized second sample to determine a level the at least autoantibody having the selected specificity, and comparing the level of the at least one autoantibody in the first sample with the level of the at least one autoantibody in the oxidized second sample. For example, wherein a lack of increase in the level of the at least one anti-phospholipid autoantibody in the oxidized second sample as compared to the level of the at least one antiphospholipid autoantibody in the first sample correlates with a neurodegenerative disease or condition in said subject.

DETAILED DESCRIPTION OF THE INVENTION

An aspect of the present invention relates to a method of diagnosing a neurodegenerative disease or condition in a subject by obtaining a sample of cerebral spinal fluid from the subject and assaying the sample to determine the presence or absence of at least one redox-reactive antiphospholipid autoantibody in said sample. Typically, the oxidized autoantibody that is detected in cerebral spinal fluid according to the method of the present invention is of IgG isotype, although other isotypes may be present before oxidation which may signal an infection in the central nervous system and/or a breech in the blood brain barrier.

Further, it has been shown that cerebral spinal fluid contains at least the following masked antiphospholipid autoantibodies: anticardiolipin (aCL), antiphosphatidylcholine (aPC), antiphosphatidylethanolamine (aPE), and, antiphosphatidylserine (aPS).

According to one embodiment of the present invention, a neurodegenerative disease or condition is diagnosed by obtaining a sample of cerebral spinal fluid from a subject and assaying the sample for an elevated level of at least one antiphospholipid autoantibody. The assay method that is used in this embodiment detects direct and indirect binding to a phospholipid (i.e. plasma protein dependent versus plasma protein independent binding), so that only autoantibodies that are in an active or unmasked form are detected and so that masked autoantibodies are not detected. In this assay, lack of autoantibodies that are in a masked form that can cause a neurodegenerative disease or condition are not detected.

An elevated level of at least one autoantibody may be determined by reference to a baseline value. For example, the baseline value may be a level of autoantibodies previously obtained from a sample from the subject at a time when the subject did not have symptoms of a neurodegenerative disease or the baseline value may be an average or mean value of a level of at least one autoantibody in a population of control individuals. For example, a baseline of antiphospholipid antibodies from 59 normal subjects is described in Sokol, D. K., et al. "Testing for antiphospholipid antibody (aPL) specificities in retrospective "normal" cerebral spinal fluid (CSF)". *Clin. Develop. Immunol.*, 11:1, March 2004, pp. 7-12.

According to another embodiment of the present invention, a neurodegenerative disease or condition is detected or diagnosed by obtaining a sample of cerebral spinal fluid from a subject, and assaying the sample to detect nitrosylated antibodies, wherein an elevated level of nitrosylated antibodies correlates with a neurodegenerative disease or condition in said subject. This method is based on findings discussed in U.S. patent application Ser. No. 11/108,826 that suggest that a conversion of antibodies from being masked autoantibodies to active antibodies takes place by nitrosylation under oxidative conditions of amino acid residues, particularly hydroxyl-containing amino acid residues such as tyrosine or tryptophane, and more particularly, tyrosine residues in and around the antibody hypervariable region, which may produce conformational changes in the antigen binding site, thus allowing antibodies that were formerly masked and unable to bind a self-antigen to become unmasked, active and capable of binding self-antigens.

The molecular characterization of antibody binding sites (paratopes) is well advanced. It has been found that there is a unique distribution of amino acids in paratopes, and in studies with 6 different antibodies, it has been found that tyrosines are the most frequent amino acids, comprising about 25% of the antigen binding sites. See, for example, Bes C., et al. "Mapping the paratope of anti-CD4 recombinant Fab 13B8.2 by combining parallel peptide synthesis and site directed mutagenesis." 2003, *J. Bio. Chem.* 278: 14265-73, and Mian S. et al. "Structure, function and properties of antibody binding sites" 1991, *J. Mol. Biol.* 217:133-151. Moreover, it has been found that radioiodination of a tyrosine residue within the binding site masks immunoreactivity of an antibody and that nitration of tyrosine within the binding site of another antibody produced an on-off switching of antibody-haptene binding. See, for example, Nikula T. K., et al. "Impact of the high tyrosine fraction in complementarity determining regions: measured and predicted effects of radioiodination on IgG immunoreactivity", *Mol. Immunol.* 1995; 32:865-872. The dominant role for tyrosine in the antibody binding site has been confirmed by Fellouse et al., "Synthetic antibodies from a four-amino-acid code: a dominant role for tyrosine in antigen recognition", *Proc Natl Acad Sci USA,* 2004; 101: 12467-72.

Therefore, it is believed that an assay to detect nitrosylated antibodies in a sample of cerebral spinal fluid can be carried out as an alternative to a binding assay for antiphospholipid autoantibodies. In this aspect of the present invention, it is not necessary to carry out a binding assay for a specific self-antigen and therefore, the method may be carried out even if the binding specificity of autoantibodies of a person having a neurodegenerative disease or condition is not known, assuming that not all autoantibodies have bound to self antigens.

The sample of cerebral spinal fluid is then assayed to detect nitrosylated antibodies. An elevated level of nitrosylated antibodies correlates with a neurodegenerative disease or condition in said subject. An elevated level of nitrosylated antibodies may be determined by reference to a baseline value. For example, the baseline value may be a level of nitrosylated antibodies previously obtained in a sample from the subject at a time when the subject did not have symptoms of a neurodegenerative disease or the baseline value may be an average or mean value of a level of nitrosylated antibodies in a population of control individuals.

Any known method of detecting nitrosylated antibodies may be used in this embodiment. For example, nitrosylated antibodies may be detected using antibodies to specific nitrosylated amino acid residues, such as to nitrotyrosine or nitrotryptophane. The sample of cerebral spinal fluid may be used directly in an assay to detect nitrosylated antibodies, or alternatively, IgG antibodies may be isolated from the sample and then the isolated antibodies may be assayed to detect nitrosylated antibodies. As a specific example, isolated IgG from a sample of cerebral spinal fluid may be coated onto ELISA plate wells, dried overnight, blocked with 1% BSA, washed and reacted with mouse anti-nitrotyrosine (1/3000, Upstate, USA, clone 1A6). After washing, alkaline phosphatase conjugated goat antimouse IgG (Sigma, St. Louis, Mo.) is added, followed by additional washing, substrate development for 2 hours at 37° C. and quantitative determinations.

In this method, the nitrosylated antibodies may be further assayed to determine whether they bind to self-antigens.

Moreover, both the method of analyzing a sample to determine the presence of antiphospholipid antibodies and the method of analyzing a sample to determine the presence of nitrosylated antibodies may both be carried out on the same subject. For example, a sample of cerebral spinal fluid may be divided into a first portion and a second portion and the first portion may be assayed for the presence of anti-phospholipid antibodies and the second portion may be analyzed for the presence of nitrosylated antibodies.

According to another aspect of the present invention, a neurodegenerative disease or condition is diagnosed in a subject by assaying a sample of cerebral spinal fluid from the subject for the presence and level of at least one autoantibody of a selected specificity, and then treating a second sample of cerebral spinal fluid from the subject with an oxidizing agent and then assaying the oxidized sample for the presence and level of the same autoantibody. In other words, the assays are carried out to determine if there is an increase in the level of a specific autoantibody or a specific set of autoantibodies after treatment with an oxidizing agent. As discussed previously, it has been found that in normal individuals, the levels of antiphospholipid autoantibodies detected in cerebral spinal fluid increases dramatically after a sample is oxidized. As also discussed above, a dramatically higher level of a wide variety of autoantibodies can be found in blood or IvIg of normal individuals that has been treated with an oxidizing agent such as hemin, in comparison with the level that is found in blood or IvIg that is untreated. As reported herein, samples of cerebral spinal fluid taken post mortem from Alzheimer's patients show no increase, or at best, only a minimal increase in detected antiphospholipid autoantibodies. These findings suggest that in a patient with a neurodegenerative disease such as Alzheimer's disease, circulating autoantibodies may have already become oxidized, unmasked and bound to targets in the nervous system. This may provide an explanation as to why there is not an increase in the level of antiphospholipid autoantibodies in the cerebral spinal fluid of patients with Alzheimer's after treatment with an oxidizing agent. In the Alzheimer's patients, the level of autoantibodies would have undergone oxidation and become depleted. Thus, according to this embodiment of the present invention, a lack of increase in the level of the at least one autoantibody in the oxidized second sample as compared to the level of the at least one autoantibody in the first sample correlates with a neurodegenerative disease or condition in said subject.

In each of the methods described above, a negative result does not rule out the presence of a neurodegenerative disease or condition. Moreover, it is not required according to the method of the invention that a positive result be diagnostic of a particular disease or condition. Rather, the methods described above may include a method wherein a positive result only indicates or strongly suggests that a neurodegenerative disease or condition exists in the subject. In particular, the presence of uncontrolled, unmasking of antiphospholipid antibodies in the central nervous system is believed to be correlated with brain pathology in view of the high content of phospholipids in brain tissue, thus providing abundant targets for such antibodies.

There is no limitation on who the subject can be in the methods described above. Typically, the subject may be selected as exhibiting physical, cognitive or radiological symptoms of a neurodegenerative disease or condition, such as, but not limited to Alzheimer's disease, Parkinson's disease, Lou Gehrig's disease, or multiple sclerosis. The subject may be one who has a family history of at least one neurodegenerative disease or condition. In such a case, the subject may be younger than, at or older than average age of onset of family members having said neurodegenerative disease or condition. The methods described above may be carried out at spaced intervals of time to determine the onset or progression of a neurodegenerative disease or condition. For example, the methods may be carried out once a year, once every five years or once every ten years in subjects who do not have symptoms of a neurodegenerative disease or condition, or may be carried out more often on subjects that exhibiting physical, cognitive or radiological symptoms of a neurodegenerative disease or condition.

The sample of cerebral spinal fluid may be obtained by any method known in the art for obtaining a sample of cerebral spinal fluid from a subject including, for example, by a spinal tap (typically, lumbar puncture).

The sample of cerebral spinal fluid may be assayed by any known method for detecting the presence of autoantibodies. For example, any known method may be used for detecting the presence of antiphospholipid autoantibodies, wherein the method detects direct or indirect binding to a phospholipid. In particular, the method of the present invention may include the detection of aCL, aPC, aPE, or aPS or a combination of these. As a non-limiting example, these autoantibodies may be detected by a binding assay such as ELISA by detecting binding with cardiolipin (CL), phosphatidylcholine (PC), phosphatidylethanolamine (PE), or phosphatidylserine (PS).

In practicing this embodiment of the method of the present invention, for determining the antibody level of an untreated sample of fluid taken from a subject, the redox state of the sample should not be altered between the step of obtaining the sample and completion of the step of assaying the sample. In other words, the assay of an untreated sample is carried out to determine self-antigen-binding antibodies that are present in active form in the sample of cerebral spinal fluid of the subject. As discussed above, it is known that the cerebral spinal fluid of normal individuals contains autoantibodies in a masked form. Therefore, care should be taken to ensure that masked autoantibodies in the cerebral spinal fluid do not become unmasked by treatment steps after the sample is obtained, leading to a false positive result, and that unmasked autoantibodies in the cerebral spinal fluid do not become masked by treatment steps after the sample is obtained, leading to a false negative result. In particular, the sample should not be exposed to oxidation or reduction (redox) conditions. Typically, normal sample handling procedures, including freezing and thawing, and typical binding assay conditions are sufficient to preserve the redox state of samples. For determining the autoantibody level of a treated sample, the sample may be treated with an oxidizing agent by any of the methods described in the publications and patent applications referenced herein. As a non-limiting example, a sample may be treated with hemin in a rocking incubator overnight at 36° C. Other oxidizing agents and other incubation temperatures may readily be determined by persons skilled in the art.

EXAMPLES

Having described the invention, the following examples are given to illustrate specific applications of the invention, including the best mode now known to perform the invention. These specific examples are not intended to limit the scope of the invention described in this application.

Example 1

Figure 1A:
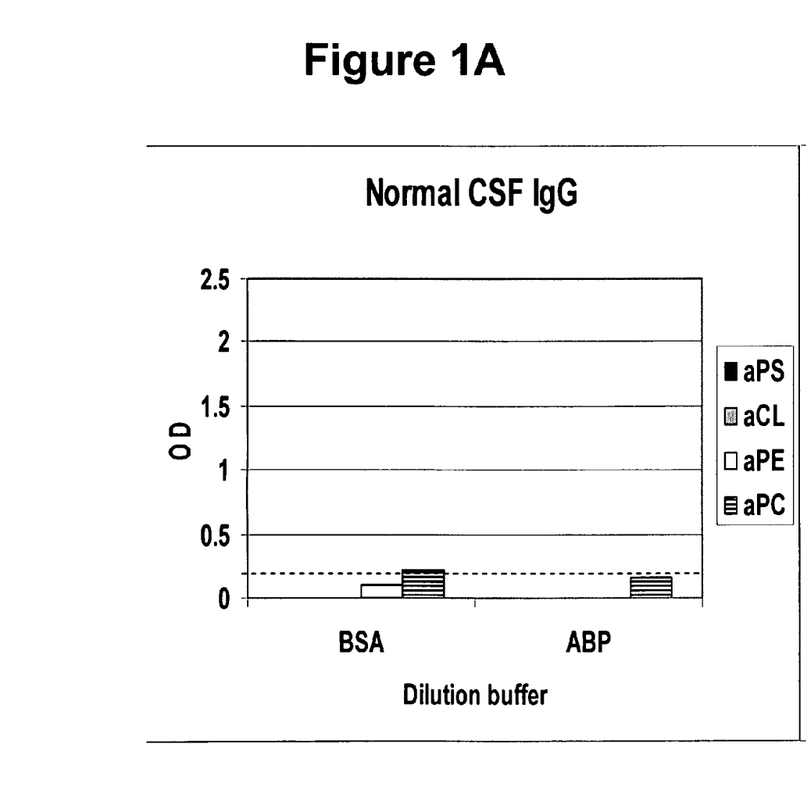
FIGS. 1A and 1B are graphs showing the level of autoantibodies detected by ELISA, for example, aPS, aCL and aPE, (as measured by optical density, OD), respectively, detected in the cerebral spinal fluid of a normal subject, for an untreated sample (FIG. 1A) and a sample that was exposed to hemin (FIG. 1B). Results are shown for both BSA-diluted and ABP-diluted samples. Dotted lines represent the positive/negative cutoff values for these autoantibodies.
Figure 1B:
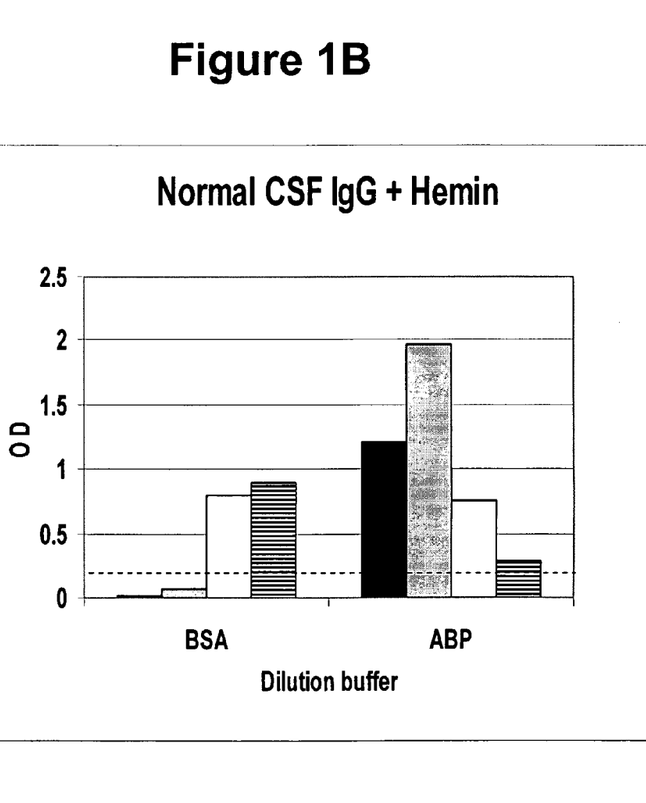

To determine whether human cerebral spinal fluid from a normal subject contains masked autoantibodies, spinal fluid was taken by spinal tap from a normal individual and samples in BSA and ABP dilution buffers were assayed by ELISA for aPS, aCL, aPE and aPC levels before and after oxidation treatment with hemin. As shown in FIGS. 1A and 1B, samples showed none or minimal levels of antiphospholipid antibodies before oxidation treatment (FIG. 1A), and substantial increases in the levels after oxidation treatment (FIG. 1B), with aPE and aPC showing the highest levels in a BSA buffer and aPS and aCL showing the highest levels in the ABP buffer.

Example 2

Figure 2:
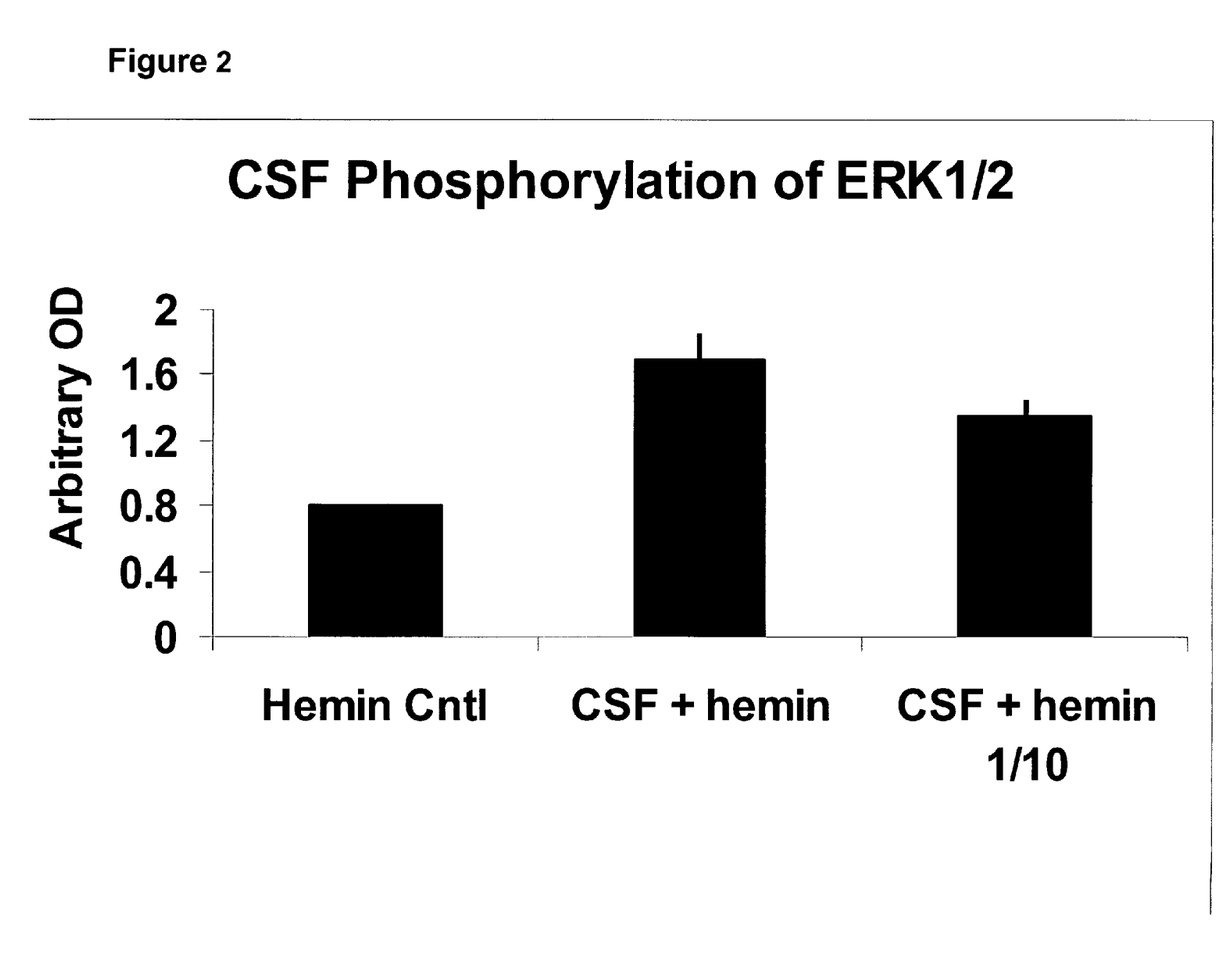
FIG. 2 is a histogram showing redox-reactive autoantibody ERK1/2 phosphorylation activity. Shown is a hemin buffer control, a hemin treated cerebral spinal fluid and a $\frac{1}{10}$ dilution of the same hemin-treated cerebral spinal fluid. These data were obtained by using a mouse neuronal model synaptosome assay. Incubation of the cerebral spinal fluid samples for 10 minutes on the synaptosomes was followed by lysing of the cells and probing for phosphorylation activity by Western blots. The degree of phosphorylation illustrated by this histogram would be sufficient to cause apoptosis of neurons.

The presence of autoantibodies sensitive to oxidation-reduction reactions in normal cerebral spinal fluid samples and their absence in Alzheimer's disease patients' spinal fluid is remarkable, albeit it does not imply that these autoantibodies are functional and/or pathogenic. To test for functional activity, the cerebral spinal fluid samples containing redox-reactive autoantibodies were tested in a mouse model synaptosome assay. Cerebral spinal fluid samples were incubated for 10 minutes on the synaptosomes followed by lysing of the cells and probing for phosphorylation activity by Western blots. FIG. 2 is a histogram showing redox-reactive autoantibody ERK1/2 phosphorylation activity of a hemin buffer control, a hemin treated cerebral spinal fluid and a 1/10 dilution of the same hemin-treated cerebral spinal fluid.

The redox-reactive autoantibodies significantly increased the phosphorylation of the members of the MAPK cascade of signal transduction molecules, thus giving these antibodies potential to interfere with normal brain cell functions. This phosphorylation kinase pathway is important for memory functions of the brain, thus implicating a role for redox-reactive autoantibodies in the pathogenesis of neurodegenerative diseases. In particular, the degree of phosphorylation illustrated by this histogram would be sufficient to cause apoptosis of neurons.

Example 3

Figure 3A:
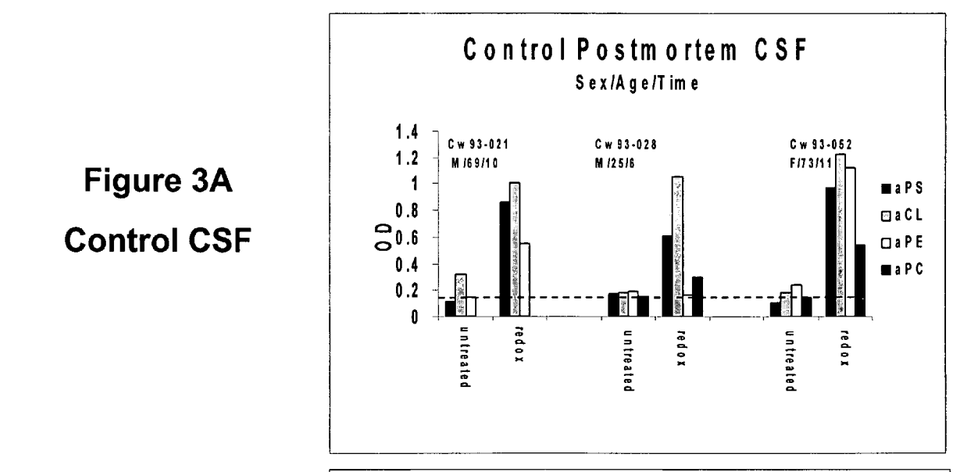
FIGS. 3A and 3B present a comparison of autoantibodies between post mortem cerebral spinal fluids (taken from brain ventricles) of 6 biopsy-confirmed Alzheimer's patients (FIG. 3B) and 3 control cerebral spinal fluid samples with no history of a neurodegenerative disease (FIG. 3A). Shown is the sex, time from death to autopsy, and age. The dotted line represents the positive/negative cutoff for antiphospholipid autoantibodies. While little positive activity is noted in the untreated samples in either the Alzheimer's or control group, the Alzheimer's samples fail to unmask redox autoantibodies when exposed to hemin.
Figure 3B:
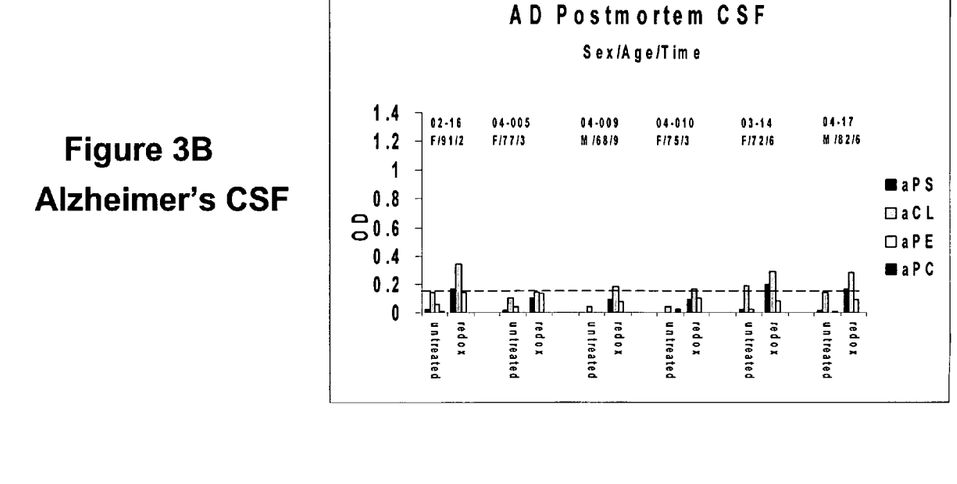

To determine whether human cerebral spinal fluid from a subject having Alzheimer's disease contains an elevated level of unmasked or active phospholipid autoantibodies, spinal fluid was taken post mortem from six patients diagnosed with Alzheimer's disease based on biopsy confirmation. Samples of cerebral spinal fluid in BSA and ABP dilution buffers were assayed for aPL levels. As shown in FIGS. 3A and 3B, samples from Alzheimer's patients (FIG. 3B) showed a decreased level or absence of aPL in comparison with the post mortem controls level (FIG. 3A) subsequent to oxidation with hemin. This indicates that oxidation-related autoantibodies have been unmasked and bound to their neuronal targets, a process shown to cause modifications in the normal synaptic mechanisms brain cells that can lead to dementia.

Example 4

An anti-nitrotyrosine assay may be conducted on IgG taken from cerebral spinal fluid of a patient having symptoms of Alzheimer's disease to determine if there is an elevated level of nitrotyrosine residues in the sample. The assay may be carried out by the methods described above. An elevated level of nitrotyrosine levels in IgG in or isolated from a cerebral spinal fluid of a subject is believed to be correlated with a neurodegenerative disease or condition in the subject.

All publications mentioned or cited herein are incorporated herein by reference in their entirety.

Obviously, many modifications and variations of the present invention are possible in light of the above teachings. It is therefore to be understood that, within the scope of the appended claims, the invention may be practiced otherwise than as specifically described.

The invention claimed is:

1. A method of screening for evidence of a neurodegenerative disease or condition in a subject, the method comprising the steps of:
   obtaining a sample of cerebral spinal fluid from the subject,
   oxidizing the sample with an oxidizing agent or electromotive force to unmask any antiphospholipid autoantibody therein;
   assaying the oxidized sample for the presence of at least one oxidized antiphospholipid autoantibody; and
   determining if there is a decrease in a level of at least one antiphospholipid autoantibody in the oxidized sample over a baseline value, wherein the baseline value is an average value of the level of the at least one oxidized antiphospholipid autoantibody in a population of control individuals, and correlating a decrease with evidence of a neurodegenerative disease or condition in said subject.

2. The method of claim 1, wherein the antiphospholipid autoantibody is anticardiolipin, antiphosphatidylcholine, antiphosphatidylethanolamine or antiphosphatidylserine.

3. The method of claim 1 wherein the antiphospholipid autoantibody is anticardiolipin.

4. The method of claim 1 wherein the subject is selected as exhibiting physical or cognitive symptoms of a neurodegenerative disease or condition.

5. The method of claim 1, wherein the neurodegenerative disease or condition is Alzheimer's disease.

6. The method of claim 1, wherein the subject is selected as exhibiting physical or cognitive symptoms of Alzheimer's disease.

7. The method of claim 1, wherein the subject has a family history of at least one neurodegenerative disease or condition.

8. The method of claim 1, wherein the subject has a family history of Alzheimer's disease.

9. The method of claim 1, wherein the subject has a family history of at least one neurodegenerative disease or condition and wherein the subject is at or beyond an average age of onset of family members having said neurodegenerative disease or condition.

* * * * *